Figure 1:
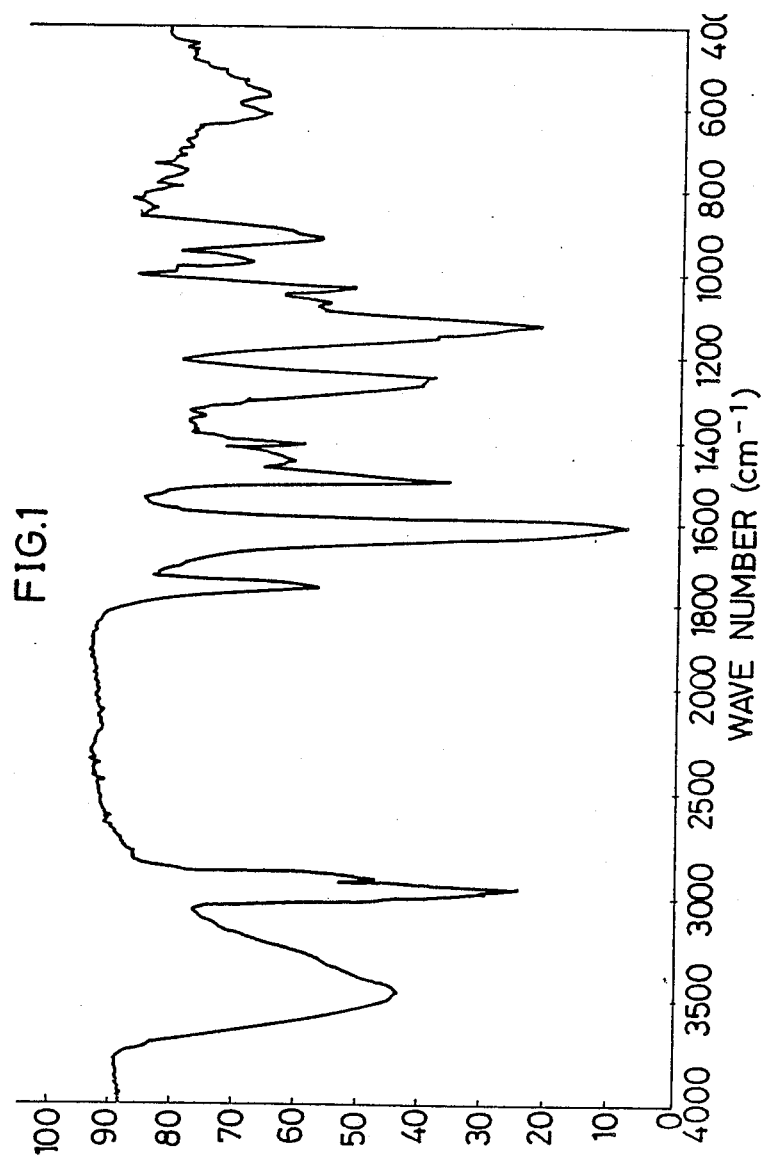

United States Patent [19]

Yamamoto et al.

[11] Patent Number: 4,914,197

[45] Date of Patent: Apr. 3, 1990

[54] NOVEL PHOSPHORIC DIESTERS

[75] Inventors: Itaru Yamamoto, Okayama; Kazumi Ogata, Toyonaka, both of Japan

[73] Assignee: Senju Pharmaceutical Co., Ltd., Osaka, Japan

[21] Appl. No.: 21,655

[22] Filed: Mar. 4, 1987

[30] Foreign Application Priority Data

Mar. 4, 1986 [JP] Japan .................................. 61-46878

[51] Int. Cl.$^4$ ...................... A61K 31/355; C07F 9/06; C07F 9/28
[52] U.S. Cl. ..................................... 536/117; 514/23; 514/100; 549/220
[58] Field of Search ........................ 549/220; 536/117; 514/23, 100

[56] References Cited

U.S. PATENT DOCUMENTS 4,564,686  1/1986  Ogata ................................. 549/220

*Primary Examiner*—Ronald W. Griffin
*Attorney, Agent, or Firm*—Burgess, Ryan and Wayne

[57] ABSTRACT

Novel phosphoric diesters of general formula:

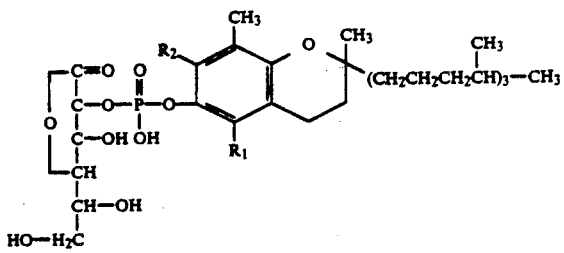

wherein $R_1$ and $R_2$ are the same or different and each means a methyl group or a hydrogen atom, provided that at least one of $R_1$ and $R_2$ is a hydrogen atom, or a salt thereof which can be produced by reacting $\beta$, $\gamma$ or $\delta$-tocopherol with a halophosphorylating agent such as phosphorus oxychloride, reacting the resultant product with ascorbic acid whereof hydroxyl groups at 5- and 6-positions are protected, and then removing protected groups from the hydroxyl groups. The phosphoric diester has antiinflammatory activity.

12 Claims, 1 Drawing Sheet

NOVEL PHOSPHORIC DIESTERS

The present invention relates to novel phosphoric diesters and salts thereof, which are useful as, for example, antiinflammatory agents, a method for production thereof, and pharmaceutical compositons containing said compounds.

A variety of antiinflammatory agents are known and it is acknowledged that steroidal antiinflammatory agents are the most effective of all. However, steroidal antiinflammatory agents have strong side effects and, therefore, present various difficulties in clinical application. Accordingly, nonsteroidal antiinflammatory agents which differ from steroidal agents in the mechanism of action have been developed and used however an effective nonsteroidal drug which is fully satisfactory in all respects has not been found.

$\beta$, $\gamma$ and $\delta$-tocopherols are known to be compounds having vitamin E activity. Ascorbic acid is known to be a medicinal substance having anti-scurvy activity and also an antioxidant for food and so on.

The diester of phosphoric acid with L-ascorbic acid and $\alpha$-tocopherol, which is structurally similar to the compound according to the present invention, is a known compound but it is only known to be a prophylactic and therapeutic agent for cataract and menopausal syndrome (U.S. Pat. No. 4,564,686).

The present inventors synthesized a variety of compounds and conducted a screening of new and highly effective nonsteroidal antiinflammatory substances. As a result, the inventors found that a compound consisting of ascorbic acid and $\beta$, $\gamma$ or $\delta$-tocopherol bound together in the form of phosphoric diester was suited to the purpose. Thus, the present invention provides a novel compound having antiinflammatory activity, a method of producing the same, and a pharmaceutical composition containing said compound.

The compound according to the present invention is a novel diester of phosphoric acid with ascorbic acid and $\beta$, $\gamma$ or $\delta$-tocopherol and has the chemical structure represented by the following general formula [I]:

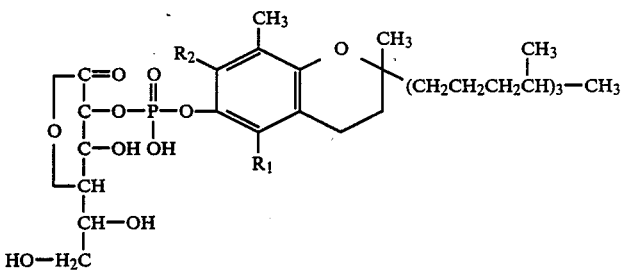

[I]

wherein $R_1$ and $R_2$ are the same or different and each represents a methyl group or a hydrogen atom, provided that at least one of $R_1$ and $R_2$ is a hydrogen atom, or a salt thereof.

One aspect of the present invention is directed to a phosphoric diester of general formula [I] or a salt thereof.

Another aspect of the present invention is directed to a method of producing a phosphoric diester of general formula [I] or a salt thereof, which comprises reacting $\beta$, $\gamma$, or $\delta$-tocopherol with a halophosphorylating agent, reacting the resulting reaction product with ascorbic acid having hydroxy-protecting groups in 5- and 6-positions, and removing said protecting groups.

In producing the compound according to the present invention, $\beta$, $\gamma$ or $\delta$-tocopherol is first reacted with a halophosphorylating agent. While the halophosphorylating agent may be any compound that can halophosphorylate the hydroxyl group of $\beta$, $\gamma$ or $\delta$-tocopherol, phosphorus oxyhalides such as phosphorus oxytrichloride, phosphorus oxytribromide, etc. can be employed with particular advantage.

The reaction proceeds with advantage in an inert solvent such as benzene, toluene or the like and in the presence of an acid acceptor. As the acid acceptor, an organic amine such as pyridine, triethylamine, etc. may be employed.

When phosphorus oxytrichloride is used as the halophosphorylating agent, the reaction may be written as follows.

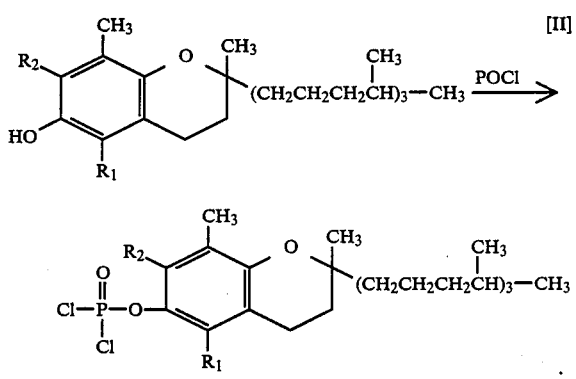

wherein $R_1$ and $R_2$ are the same or different and each represents a methyl group or a hydrogen atom, provided that at least one of $R_1$ and $R_2$ is a hydrogen atom.

The $\beta$, $\gamma$ or $\delta$-tocopherol employed as a reactant may be either of the DL-compound or the D-compound. Thus, the reaction proceeds in the same manner and the yield is the same.

In the present invention, the reaction product thus obtained (formula [II]) is then reacted with ascorbic acid having hydroxy-protecting groups in 5- and 6-positions. For this reaction, the above-mentioned compound [II] may be isolated from the reaction mixture or, if desired, the reaction mixture may be directly subjected to reaction with ascorbic acid. With regard to protective groups for hydroxyl groups in the 5- and 6-positions of ascorbic acid, various groups are known in the field of ascorbic acid chemistry and one selected from among such groups may be employed for the purposes of the invention. Among such protective groups are isopropylidene group, acyl groups such as acetyl, and so on. Most generally, an isopropylidene group is employed. The reaction proceeds readily in an appropriate inert organic solvent. As the solvent, it is generally preferable to employ a nonpolar solvent such as tetrahydrofuran, acetonitrile or the like but any other solvent that does not interfere with the reaction may likewise be employed. The reaction proceeds readily in the presence of an acid acceptor. The preferred acid acceptor is a tertiary amine such as pyridine, triethylamine and so on. The reaction for elimination of the protective group is conducted under mild conditions. For example, by making the reaction mixture acidic, the protective group can be easily eliminated. For this acidification, a suitable inorganic acid such as hydrochloric acid, phosphoric acid, sulfuric acid, etc. or an organic acid such as acetic acid, citric acid, etc. may be employed.

The above procedure gives the compound [I] according to the present invention.

In terms of crystallinity, the compound according to the present invention is preferably in the salt form rather than in the free acid form. Among the salts, the sodium salt and potassium salt, of instance, are readily soluble in water but the calcium salt is insoluble. For convertion of the free acid to a salt, neutralization is the easiest and generally the most suitable procedure.

The compound according to the present invention is useful as a nonsteroidal antiinflammatory agent.

The compound is stable at room temperature and can be formulated in the form of free acid or a pharmacologically acceptale salt into suitable medicinal composition by the established pharmaceutical procedures. The term "composition" as used herein means any and all of sterile injectable products, ophthalmic products, tablets, capsules, ointments, creams, poultices and other preparations.

While the amount of compound [I] in such a pharmaceutical composition depends on dosage form, symptom, and so on, the compound is incorporated generally in a proportion of about 0.005 to 30 w/v percent and preferably about 0.01 to 10 w/v percent. Taking an injection as an example, an aqueous solution containing about 0.01 to 0.1 w/v percent of the compound may be provided. In the case of an ointment, it may contain about 1 to 10 w/w percent of the compound. As to peroral dosage forms, about 100 to 1000 mg per day per adult may be formulated.

The antiinflammatory compositions according to the present invention may contain various other agents and substances. Such agents or substances include preservatives, excipients, nonionic surfactants, and so on and unless the object of the present invention are not interferred with, other suitable drugs, colorants, etc. may also be incorporated.

The phosphoric diester of ascorbic acid and $\beta$, $\gamma$ or $\delta$-tocopherol according to the present invention can be used with advantage as an ingredient in pharmaceutical preparations and cosmetic products. If the phosphoric ester bonds are cleaved by phosphatase or the like in vivo, the compound yields vitamin C and the corresponding tocopherol active substance so that no toxic metabolites are produced, thus presenting no safety problem.

Referring to the drawing, FIG. 1 shows the infrared absorption spectrum of L-ascorbyl D-$\delta$-tocopherol phosphate sodium.

The following examples and experimental examples are further illustrative of the present invention.

EXAMPLE 1

L-ascorbyl DL-$\beta$-tocopherol phosphate [general formula (1) wherein $R_1$=methyl, $R_2$=H] sodium In 30 ml of benzene was dissolved 3 g of phosphorus oxytrichloride, and a mixed solution of 4.2 g (0.01 mole) of DL-$\beta$-tocopherol and 4 g of pyridine in 20 ml of benzene was added dropwise with stirring. After completion of dropwise addition, the mixture was further stirred for 3 hours and the precipitated pyridine hydrochloride was filtered off. The filtrate was then concentrated under reduced pressure and 20 ml of benzene was added to the oily residue.

On the other hand, 2.6 g (0.012 mole) of 5,6-isopropylidene-protected ascorbic acid prepared by acetonization of L-ascorbic acid and 2 g of pyridine were dissolved in 60 ml of tetrahydrofuran (THF) and the above benzene solution was added dropwise with stirring. After completion of dropwise addition, the mixture was stirred for about 1 hour and the precipitated pyridine hydrochloridewas filtered off. The filtrate was concentrated under reduced pressure to remove the solvent. The resulting oil was dissolved in 15 ml of ethyl alcohol and after addition of 75 ml of 1N-hydrochloric acid, the solution was refluxed for about 15 minutes. After cooling, the reaction mixture was extracted with ethyl acetate and dried over anhydrous sodium sulfate. The ethyl acetate was then distilled off to give crude free acid as a residue.

This crude free acid was dissolved in about 100 ml of ethyl alcohol and, then, a solution of potassium hydroxide in ethyl alcohol was gradually added in droplets until the pH of the solution became neutral, whereupon slightly brownish white crystals separated out. The crystals were collected by filtration to give the potassium salt.

The above potassium salt was dissolved in 100 ml of water and the solution was acidified with hydrochloric acid and extracted with ethyl acetate. The extract was dried over anhydrous $Na_2SO_4$ and the ethyl acetate was distilled off to give the free acid as a light yellow amorphous solid. This solid was dissolved in 80 ml of ethyl alcohol and a solution of sodium hydroxide in the alcohol was added dropwise until the solution became neutral, whereupon white crystals separated out.

The crystals were collected by filtration and recrystallized from tetrahydrofuran-ethyl alcohol to give 3.2 g (45.0%) of white powdery crystals. The UV spectrum of this product shows absorptions around 200, 220 and 257 nm (in water).

Melting point: Carbonization begins gradually around 210° C.

Elemental analysis: (for $C_{34}H_{53}O_{10}PNa_2 \cdot H_2O$) Calcd. C, 56.97% H, 7.73%. Found C, 56.77% H, 7.75%.

EXAMPLE 2

L-Ascorbyl DL-$\gamma$-tocopherol phosphate [general formula (1) wherein $R_1$=H; $R_2$=methyl] sodium In the same manner as Example 1, the above compound was obtained as white powdery crystals in a yield of 55%.

m.p.: Carbonization begins gradually around 200° C.

Elemental analysis: for $C_{34}H_{53}O_{10}PNa_2 \cdot H_2O$ Calcd. C, 56.97% H, 7.73%. Found C, 56.88% H, 7.65%.

EXAMPLE 3

L-Ascorbyl D-δ-tocopheryl phosphate [general formula (1) wherein $R_1$ and $R_2$ each=H] sodium In the same manner as Example 1, the above compound has synthesized as white powdery crystals in a yield of 48%.

$[\alpha]_D^{24}+45.8°$ (C=1.0, $H_2O$).

m.p.: Carbonization begins gradually around 210° C.

Elemental analysis: for $C_{33}H_{51}O_{10}PNa_2.H_2O$ Calcd. C, 56.40% H, 7.60%. Found C, 56.60% H, 7.41%.

The infrared absorption spectrum (KBr) of this product is shown in FIG. 1.

EXPERIMENTAL EXAMPLE 1

(Topical Antiinflammatory Effect)

The antiinflammatory effect of the compound according to the present invention was investigated in the anterior chamber paracentesis inflammation model of the rabbits eye.

Method: Using female white rabbits, a 0.1% ophthalmic solution of L-ascorbyl tocopheryl phosphate sodium and, as a control, physiological saline were instilled into the bilateral eyes of rabbits in volumes of 10 µl each at 2, 1 and 0.5 hour before peracentesis and using a 27-gauge needle about 200 µl of anterior chamber aqueous humor was collected from each eye (primary aqueous humor). Then, after an interval of 1.5 hours, the aqueous humor was collected again in the same manner (secondary aqueous humor). The protein content of each aqueous sample was determined by the method of Lowry and the increases in the amount of protein (protein content of secondary aqueous humor-protein content of primary aqueous humor) in the respective groups were compared to evaluate the antiinflammatory effect of each test substance.

Results: The increase in the amount of protein in secondary aqueous humor in each group is shown in Table 1. Compared with the control group, the compound according to the present invention showed a significant antiinflammatory effect.

TABLE 1

| Group | Increase in protein | % Inhibition | Number of eyes |
|---|---|---|---|
| Control | 25.5 | — | 10 |
| β-EPC | 16.0 | 37.3 | 6 |
| γ-EPC | 16.2 | 36.5 | 6 |
| δ-EPC | 15.3 | 40.0 | 8 |
| DEX | 20.8 | 18.4 | 6 |

β-EPC:L-acorbyl DL-β-tocopheryl phosphate sodium
γ-EPC:L-ascorbyl DL-γ-tocopheryl phosphate sodium
δ-EPC:L-ascorbyl D-δ-tocopheryl phosphate sodium
DEX:0.1% Dexamethasone ophthalmic solution

EXPERIMENTAL EXAMPLE 2

(Inhibitory Effect on Ultraviolet-Induced Erythema)

Method: The back hairs of Hartly guinea pigs were clipped with an electric clipper and shaved with an electric razor. Then, a cloth with two holes 11 mm in diameter and 4 cm apart was appliedto the back for positioning and a 1 (w/v) % aqueous solution of δ-EPC (adjusted to pH 6.0) and, as control, water were applied 3 times in 100 µl portions each at 1-hour intervals around the sites of said holes over an area 4 cm in diameter. One hour after the final application, said cloth with small holes was applied again and the exposed skin areas was irradiated with ultraviolet rays at 1700 luxes for 360 seconds. Then, after 1 and 2 hours, respectively, the back was grossly examined for erythema.

| | |
|---|---|
| No erythema | 0 |
| Slight erythema | 1 |
| Erythema without a distinct margin | 2 |
| Erythema with a distinct margin | 3 |

Results: The degrees of erythema on both sides of the back of guinea pigs are shown in Table 2.

TABLE 2

| Group | After 1 hour | | After 2 hours | |
|---|---|---|---|---|
| | Right | Left | Right | Left |
| Control | 2 | 2 | 2 | 2 |
| | 3 | 2 | 3 | 2 |
| | 2 | 2 | 2 | 2 |
| | 2 | 2 | 2 | 2 |
| δ-EPC | 1 | 0 | 1 | 0 |
| | 1 | 1 | 1 | 1 |
| | 1 | 1 | 1 | 1 |
| | 1 | 1 | 1 | 1 |

Result: Compared with the control group, δ-EPC showed a significant antiinflammatory effect.

PREPARATION EXAMPLE 1

Ophthalmic Solution for Topical Application

| | |
|---|---|
| L-Ascorbyl DL-β-tocopheryl phosphate sodium | 0.1 g |
| Boric acid | 1.5 g |
| Borax | 0.3 g |
| Methyl P-hydroxybenzoate | 0.026 g |
| Propyl P-hydroxybenzoate | 0.014 g |
| Sterile pure water | To make 100 ml |

According to the above formula, an ophthalmic solution was prepared in accordance with the established pharmaceutical procedure.

PREPARATION EXAMPLE 2

Peroral Tablets

| | |
|---|---|
| L-Ascorbyl DL-β-tocopheryl phosphate sodium | 100 mg |
| Lactose | 80 mg |
| Starch | 17 mg |
| Magnesium stearate | 3 mg |

Using the above formulation for 6 tablets, tablets for oral administration are prepared in accordance with the established pharmaceutical procedure. The tablets may be sugar-coated.

PREPARATION EXAMPLE 3

Injectable Solution

| | |
|---|---|
| L-Ascorbyl DL-δ-tocopheryl phosphate sodium | 0.02 g |
| Glucose | 5 g |
| Distilled water for injection | To make 100 ml |

Using the above formula, an injectable solution is prepared by the established pharmaceutical procedure for sterile products.

PREPARATION EXAMPLE 4

Dermatological Ointment for External Application

| | |
|---|---|
| L-Ascorbyl DL-γ-tocopheryl phosphate sodium | 5.0 g |
| Glycerin | 12.0 g |
| Stearyl alcohol | 25.0 g |
| White petrolatum | 25.0 g |
| Methyl P-hydroxybenzoate | 0.025 g |
| Propyl P-hydroxybenzoate | 0.015 g |
| Sterile pure water | To make 100 g |

Using the above formula, a dermatological ointment for external application is prepared in accordance with the established pharmaceutical procedure for ointments.

PREPARATION EXAMPLE 5

Syrup

| | |
|---|---|
| L-Ascorbyl DL-δ-tocopheryl phosphate sodium | 2.0 g |
| D-Sorbitol, 70% soln. | 70 ml |
| Methyl P-hydroxybenzoate | 0.028 g |
| Butyl P-hydroxybenzoate | 0.012 g |

The above ingredients are dissolved in sterile pure water, adjusted to pH 6.0 with 1N-HCl, diluted to a total of 100 ml, and filtered. The filtered solution is filled into a glass bottle to provide a syrup.

PREPARATION EXAMPLE 6

Cosmetic Lotion

| | |
|---|---|
| L-Ascorbyl DL-β-tocopheryl phosphate potassium | 1.0 g |
| Citric acid | 0.1 g |
| Glycerin | 5.0 g |
| Ethyl alcohol | 8.0 ml |
| Methyl P-hydroxybenzoate | 0.1 g |

The above ingredients are dissolved in sterile pure water, adjusted to pH 6.0 with 1N-sodium hydroxide, made up to a total of 100 ml, and filtered. The filtered solution is filled into a glass bottle to provide a cosmetic lotion.

PREPARATION EXAMPLE 7

Cream

| | |
|---|---|
| L-Ascorbyl D-δ-tocopheryl phosphate sodium | 1.0 g |
| Stearic acid | 2.0 g |
| Stearyl alcohol | 7.0 g |
| Squalane | 5.0 g |
| Octyldodecanol | 6.0 g |
| Polyoxyethylene (15) cetyl ether | 3.0 g |
| Glycerin monostearate | 2.0 g |
| Propylene glycol | 5.0 g |
| Methyl P-hydroxybenzoate | 0.2 g |
| Propyl P-hydroxybenzoate | 0.1 g |
| Sterile pure water | To make 68.7 g |

In sterile pure water are dissolved propylene glycol and L-ascorbyl D-δ-tocopheryl phosphate sodium and the solution is warmed to 70° C. The other ingredients are mixed and warmed to 70° C. Then, with stirring at the same temperature, the above aqueous solution is added and the mixture is homogenized well and cooled to room temperature. It is then transferred into a cream container to provide a cosmetic cream.

We claim:

1. A phosphoric diester of general formula:

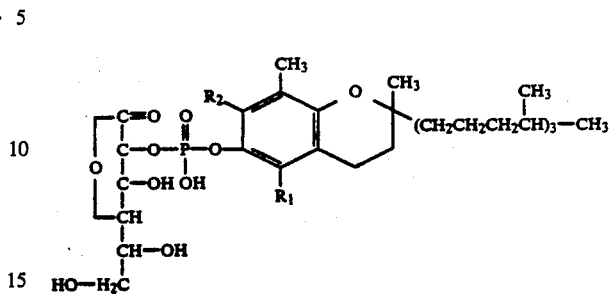

wherein $R_1$ and $R_2$ are the same or different and each represents a methyl group or a hydrogen atom, provided that at least one of $R_1$ and $R_2$ is a hydrogen atom, or a salt thereof.

2. A phosphoric diester or a salt thereof according to claim 1, wherein $R_1$ is a methyl group and $R_2$ is a hydrogen atom.

3. A phosphoric diester of a salt thereof according to claim 1, wherein $R_1$ is a hydrogen atom and $R_2$ is a methyl group.

4. A phosphoric diester or a salt thereof according to claim 1, wherein each of $R_1$ and $R_2$ is a hydrogen atom.

5. A pharmaceutical composition useful as an anti-inflammatory agent and comprised of a therapeutically effective amount of a compound represented by the formula:

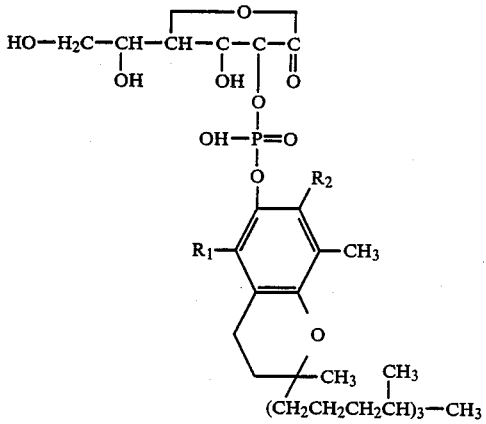

wherein $R_1$ and $R_2$ are the same or different and each represents a methyl group or a hydrogen atom, provided that at least one of $R_1$ and $R_2$ is a hydrogen atom, or a salt thereof, and a carrier.

6. The pharmaceutical composition of claim 5, wherein $R_1$ is a methyl group and $R_2$ is a hydrogen atom.

7. The pharmaceutical composition of claim 5, wherein $R_1$ is a hydrogen atom and $R_2$ is a methyl group.

8. The pharmaceutical composition of claim 5, wherein each of $R_1$ and $R_2$ is a hydrogen atom.

9. A method of imparting an anti-inflammatory effect in a subject in need of such treatment, which comprises administering to said subject an anti-inflammatory effective amount of the pharmaceutical composition of claim 5.

10. A method of imparting an anti-inflammatory effect in a subject in need of such treatment, which comprises administering to said subject an anti-inflammatory effective amount of the pharmaceutical composition of claim 6.

11. A method of imparting an anti-inflammatory effect in a subject in need of such treatment, which comprises administering to said subject an anti-inflammatory effective amount of the pharmaceutical composition of claim 7.

12. A method of imparting an anti-inflammatory effect in a subject in need of such treatment, which comprises administering to said subject an anti-inflammatory effective amount of the pharmaceutical composition of claim 8.

* * * * *